United States Patent [19]

Sterzel et al.

[11] Patent Number: 4,840,960

[45] Date of Patent: Jun. 20, 1989

[54] TREATMENT OF GLOMERULONEPHRITIS

[75] Inventors: R. Bernd Sterzel; Alexander Scriabine, both of Guilford, Conn.

[73] Assignee: Miles Laboratories, Inc., Elkhart, Ind.

[21] Appl. No.: 89,094

[22] Filed: Aug. 25, 1987

[51] Int. Cl.$^4$ ............................................. A61K 31/44
[52] U.S. Cl. ..................................................... 514/356
[58] Field of Search ........................................ 514/356

[56] References Cited

U.S. PATENT DOCUMENTS 4,582,840  4/1986  Garthoff et al. ..................... 514/356

OTHER PUBLICATIONS

*Taber's Cyclopedic Medical Dictionary*, 11th Ed. (1970) p. G23.
B. M. Brenner, "Nephron Adaptation of Renal Injury or Ablation", *Am. J. Physiol.*, (1985), 249, F324–F337.
T. H. Hostetter, J. L. Olson, H. G. Rennke, M. A. Venkatachalam, B. M. Brenner, "Hyperfiltration in Remnant Nephrons: A Potentially Adverse Response to Renal Ablation", *Am. J. Physiol.*, (1981), 241, F185–F193.
R. Loutzenhiser, M. Epstein, "Effects of Calcium Anatagonists on Renal Hemodynamics", (Editorial Review), *Am. J. Physiol.*, (1985), 249, F619–F629.
A. Fleckenstein, M. Frey, J. Zorn, G. Fleckenstein–Gruen, "Experimental Basis for Long-Term Therapy of Arterial Hypertension with Calcium Anatagonists", *Am. J. Cardiol.*, (1985), 56, 3H–14H.
I. Ichikawa, J. F. Miele, B. M. Brenner, "Reversal of Renal Cortical Actions of Angiotension II", by Verapamil and Manganese, *Kidney Int.*, (1979), 16, 136–147.
B. Wright, I. Zeidman, R Greig, G. Poste, "Inhibition of Macro Phage Activation by Calcium Channel Blockers and Calmodulin Antagonists", *Cell Immunol.*, (1985), 95, 46–53.
J. L. Mehta, "Influence of Calcium Channel Blockers on Platelet Function and Arachidonic Acid Metabolism", *Am. J. Cardiol.*, (1985), 56, 158B–164B.
E. Jouvin-Marche, J. Cerrina, E. Coeffier, P. Duroux, J. Benveniste, "Effect of the $Ca^{2+}$-Antagonist Nifedipine on the Release of Platelet-Activating Factor (PAF-Acether), Slow-Reacting Substance and Beta--Glucuronidase from Human Neutrophilis", *Eur. J. Pharmacol.*, (1983), 89, 19–26.
H. Heinle, A. Reich, "Inhibition by Verapamil of the Medium Change Induced Stimulation of Cultured Vascular Smooth Muscle Cells", *Arzneim Forsch,* (1985), 35, 1811–1812.
W. W. Busse, C. A. Swenson and R. M. Bedard, *J. Lab. Clin. Med.*, 109, 422–428, (1987).

*Primary Examiner*—Douglas W. Robinson
*Assistant Examiner*—R. Kearse
*Attorney, Agent, or Firm*—Sprung Horn Kramer & Woods

[57] ABSTRACT

A method for treating a patient suffering from glomerulonephritis comprising administering to the patient an effective amount of nitrendipine.

6 Claims, 4 Drawing Sheets

TREATMENT OF GLOMERULONEPHRITIS

BACKGROUND OF THE INVENTION

1. Field of the Invention

The present invention concerns the treatment of glomerulonephritis. More particularly, this invention is directed to treating patients suffering from glomerulonephritis by administering to such patients an effective amount of nitrendipine.

2. Background Information

Glomerulonephritis, an immune complex disease, is often a poststreptococcal disease.

Glomerulonephritis may be initiated by antigen-antibody complexes on the glomerular basement membrane. The most important antigen is probably in the streptococcal protoplast membrane. In acute nephritis, there is blood and protein in the urine, edema, high blood pressure, and nitrogen retention; serum complement levels are low. A few patients die; some develop chronic glomerulonephritis with ultimate kidney failure; the majority recover completely.

At present, no rational treatment is available for progressive glomerular disease. Strategies for protective intervention should be based upon knowledge of etiologic and pathogenetic factors that determine the course of the glomerular lesions. While such information is currently fragmented or lacking, it appears reasonable to consider that the progressive glomerular changes are the result of an ongoing inflammatory response to injury of glomerular structures.

The initiating types of injury to the glomerulus may be immunological, metabolic, toxic, or physical in nature. In states of loss of functioning nephrons, glomerular hypertension has been suggested to be a pathogenetic factor that contributes to the perpetuation of glomerular injury, no matter of what initial etiology (Brenner, B. M., "Nephron Adaptation of Renal Injury or Ablation.", Am. J. Physiol., (1985), 249, F324–F337).

Elevation of glomerular capillary hydraulic pressure ($P_{GC}$) has been shown to occur as a compensatory mechanism to maintain overall glomerular filtration (Brenner, supra; Hostetter, T. H., Olson J. L., Rennke, H. G., Venkatachalam, M. A., Brenner, B. M., "Hyperfilitration in Remnant Nephrons: A Potentially Adverse Response to Renal Ablation", Am. J. Physiol., (1981), 241, F185–F193).

In analogy to the injurious effects of increased blood pressure on arterial and arteriolar walls, glomerular hypertension has been considered to damage the glomerulus in an as yet ill-defined manner. Conceptually, the continued proliferation of glomerular cells and extracellular matrix constitute the inflamatory response to such injury. Among the cells that may participate in this response one should consider the glomerular endothelial, mesangial, and epithelial cells, as well as blood-derived cells, e.g., leukocytes and platelets.

A rational for the use of calcium entry blockers (CEB) for protective intervention in progressive glomerular disease is based on several actions of this group of agents documented in other cell systems. First, CEB have general vasodilatory effects (Loutzenhiser, R., Epstein, M., "Effects of Calcium Anatagonists on Renal Hemodynamics", (Editorial review)., Am. J. Physiol., (1985), 249, F619–F629; Fleckenstein, A., Frey, M., Zorn, J., Fleckenstein-Gruen, G., "Experimental Basis for Long-Term Therapy of Arterial Hypertension with Calcium Anatagonists", Am. J. Cardiol., (1985), 56, 3H–14H).

In particular, CEB have been shown to normalize $P_{GC}$ after it had been raised by infusion of angiotensin II(Ichikawa, I., Miele, J. F., Brenner, B. M., "Reversal of Renal Cortical Actions of Angiotensin II by Verapamil and Manganese, Kidney Int., (1979), 16, 136–147).

Second, recent cell culture studies have revealed that CEB may interfere with the activation of macrophages (Wright, B., Zeidman, I., Greig, R., Poste, G., "Inhibition of Macro Phage Activation by Calcium Channel Blockers and Calmodulin Antagonists", Cell Immunol., (1985), 95, 46–53) and platelets (Mehta, J. L., "Influence of Calcium Channel Blockers on Platelet Function and Arachidonic Acid Metabolism", Am. J. Cardiol., (1985), 56, 158B–164B).

Third, the release of platelet activating factor, a powerful inflammatory mediator, from leukocytes has been found suppressed in the presence of CEB (Jouvin-Marche, E., Cerrina, J., Coeffier, E., Duroux, P., Benveniste, J., "Effect of the $Ca^{2+}$-antagonist Nifedipine on the Release of Platelet-activating Factor (PAF-acether), Slow-Reacting Substance and Beta-glucuronidase from Human Neutrophilis", Eur. J. Pharmacol., (1983), 89, 19–26).

Fourth, recent work by Heinle and Reich has indicated that the CEB, verapamil, prevents growth-promoting effects of serum on cultured vascular smooth muscle cells (Heinle, H., Reich A., "Inhibition by Verapamil of the Medium Change Induced Stimulation of Cultured Vascular Smooth Muscle Cells", Arzneim Forsch, (1985), 35, 1811–1812).

According to a recent publication by Busse et al. (J. Lab. Clin. Med., 109, 422–428, (1987)), nitrendipine inhibits ragweed antigen E.-dependent basophil histamine release.

SUMMARY OF THE PRESENT INVENTION

The present invention concerns treating patients, e.g., mammals, including humans, suffering from glomerulonephritis, by administering to such patient an effective amount of nitrendipine, either alone or in admixture with a diluent or in the form of a medicament.

DETAILED DESCRIPTION OF THE INVENTION

Nitrendipine has the following formula

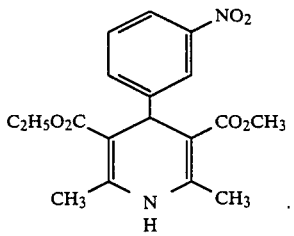

Figure 1:
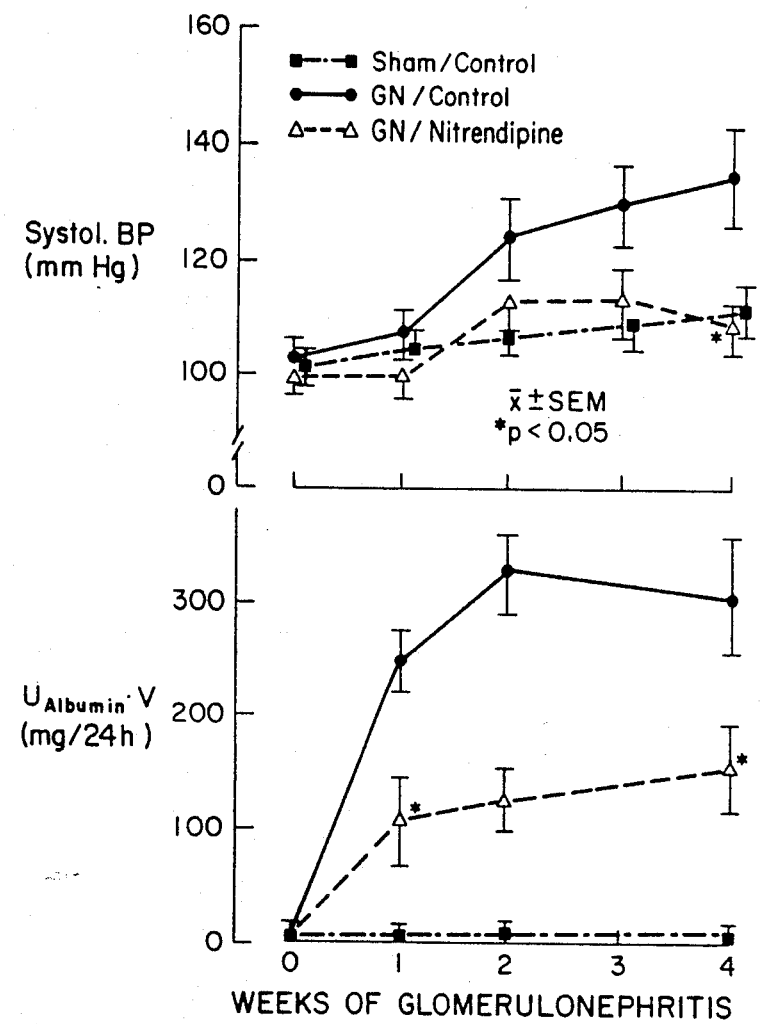
FIG. 1 depicts in two plots the time course of systolic blood pressure (FIG. 1a) and urinary albumin excretion (FIG. 1b) in nephritic rats (GN) and sham rats on pellets with or without nitrendipine.

"Medicament" as used herein means physically discrete coherent portions suitable for medical administration. "Medicament in dosage unit form" as used herein means physically discrete coherent units suitable for medical administration, each containing a daily dose or a multiple (up to four times) or a sub-multiple (down to a fortieth) of a daily dose of nitrendipine in association with a carrier and/or enclosed with an envelope. Whether the medicament contains a daily dose, or for example, a half, a third or a quarter of a daily dose will depend on whether the medicament is to be administered once or, for example, twice, three times or four times a day, respectively.

The pharmaceutical compositions for use according to the invention may, for example, take the form of suspensions, solutions and emulsions of nitrendipine in aqueous or non-aqueous diluents, syrups, granulates or powders.

The diluents to be used in pharmaceutical compositions (e.g., granulates) adapted to be formed into tablets, dragees, capsules, caplets and pills include the following: (a) fillers and extenders, e.g., starch, sugars, mannitol and silicic acid; (b) binding agents, e.g., carboxymethyl cellulose and other cellulose derivatives, algi-nates, gelatine and polyvinyl pyrrolidone; (c) moisturizing agents, e.g., glycerol; (d) disintegrating agents, e.g., agaragar, calcium carbonate and sodium bicarbonate; (e) agents for retarding dissolution, e.g., paraffin; (f) resorption accelerators, e.g., quaternary ammonium compounds; (g) surface active agents, e.g., cetyl alcohol, glycerol monostearate; (h) adsorptive carriers, e.g., kaolin and bentonite; (i) lubricants, e.g., talc, calcium and magnesium stearate and solid polyethyl glycols.

The tablets, dragees, capsules, caplets and pills formed from the pharmaceutical compositions of the invention can have the customary coating, envelopes and protective matrices, which may contain opacifiers. They can be so constituted that they release the active ingredient only or preferably in a particular part of the intestinal tract, possibly over a period of time. The coatings, envelopes and protective matrices may be made, for example, from polymeric substances or waxes.

Nitrendipine can also be made up in microencapsulated form together, with one or several of the above-mentioned diulents.

The diluents to be used in pharmaceutical compositions adapted to be formed into suppositories can, for example, be the usual water-soluble diluents, such as polyethylene glycols and fats (e.g., cocoa oil and high esters, [e.g., $C_{14}$-alcohol with $C_{16}$-fatty acid]) or mixtures of these diluents.

The pharmaceutical compositions which are solutions and emulsions can, for example, contain the customary diluents (with, of course, the above-mentioned exclusion of solvents having a molecular weight below 200, except in the presence of a surface-active agent), such as solvents, dissolving agents and emulsifiers. Specific non-limiting examples of such diluents are water, ethyl alcohol, benzyl benzoate, propylene glycol, 1,3-butylene glycol, dimethylformamide, oils (for example, ground nut oil), glycerol, tetrahydrofurfuryl alcohol, polyethylene glycols and fatty acid esters of sorbitol or mixtures thereof.

For parenteral administration, solutions and emulsions should be sterile and, if appropriate, blood-isotonic.

The pharmaceutical compositions which are suspensions can contain the usual diluents, such as liquid diluents, e.g., water, ethyl alcohol, propylene glycol, surface-active agents (e.g, ethoxylated isostearyl alcohols, polyoxyethylene sorbite and sorbitane esters) microcrystalline cellulose, aluminium metahydroxide, bentonite, agar-agar and tragacanth or mixtures thereof.

All the pharmaceutical compositions according to the invention can also contain coloring agents and presevatives, as well as perfumes and flavoring additions (e.g., peppermint oil and eucalyptus oil) and sweetening agents (e.g., saccharin and aspartame).

The pharmaceutical compositions for use according to the invention generally contain from 0.5 to 90% of nitrendipine by weight of the total composition.

In addition to nitrendipine, the pharmaceutical compositions and medicaments for use according to the invention can also contain other pharmaceutically active compounds.

Any diluent in the medicaments for use in of the present invention may be any of those mentioned above in relation to the pharmaceutical compositions for use in the present invention. Such medicaments may include solvents of molecular weight less than 200 as the sole diluent.

The discrete coherent portions constituting medicaments for use according to the invention will generally be adapted by virtue of their shape or packaging for medical administration and may be, for example, any of the following: tablets (including lozenges and granulates), pills, dragees, capsules, caplets, suppositories and ampoules. Some of these forms may be made up for delayed release of the active ingredient. Some, such as capsules and caplets, may include a protective envelope which renders the portions of the medicament physically discrete and coherent.

The preferred daily dose for administration of the medicaments for use in the invention is 0.1 to 6 mg of nitrendipine in the case of intravenous administration and 5 to 80 mg of nitrendipine in the case of oral administration.

The product of the above-mentioned pharmaceutical compositions and medicaments is carried out be any method know in the art, for example, by mixing nitrendipine with the diluents(s) to form a pharmaceutical composition (e.g., a granulate) and then forming the composition into the medicament (e.g. tablets).

It is envisaged that nitrendipine will be administered perorally, parenterally (for example, intramuscularly, intraperitoneally, subcutaneously or intravenously), rectally or locally, preferably orally or parenterally, especially perlingually or intravenously. Preferred pharmaceutical compositions and medicaments are, therefore, those adapted for administration such as oral or parenteral administration. Administration in the method of the invention is preferably oral or parenteral administration.

Nitrendipine is considerably more potent by intravenous than by oral administration. Oral doses in humans are likely to vary from 5 to 40 mg, either once or twice a day. By intravenous administration, nitrendipine can be expected to be effective at total doses ranging from 0.1 to 3 mg, once or twice a day. If human doses are expressed per kg of body weight, the dose should range from 0.0014 to 0.043 mg/kg intravenously or 0.07 to 0.6 mg/kg orally. In some animal species (e.g., rats) the oral doses on per kg body weight basis will be considerably higher (e.g., 2 to 80 mg/kg). Nevertheless, it can at times be necessary to deviate from the above dosage rates, and in particular to do so as a function of the nature and body weight of the human or animal subject to be treated, the individual reaction of this subject to the treatment, type of formulation in which the active ingredient is administered, the mode in which the administration is carried out and the point in the progress of the disease or interval at which it is to be administered. Thus, it may in some case suffice to use less than the above-mentioned minimum dosage rate, while other cases the upper limit mentioned must be exceeded to achieve the desired results. Where larger amounts are administered, it may be advisable to divide these into several individual administrations over the course of he day.

The invention will now be described with reference to the following non-limiting examples.

EXAMPLES

Experimental protocol

The accelerated mode of antiglomerular basement membrane (AGBM) glomerulonephritis (BH) was used, as described in Foellmer, H. D., Sterzel, R. B., Kashgarian, M., "Progressive Glomerular Sclerosis in Experimental Anti-GBM Glomerulonephritis", *Am. J. Kidney Dis.*, (1986), 7, 5-12; Stein, H. D., Sterzel, R. B., Hunt, J. D., Pabst, R., Kashgarian, M., "No -aggravation of the Course of Experimental Glomerulonephritis in Spontaneously Hypertensive Rats", *Am. J. Pathol.*, (1986), 122, 520-528.

Male Wistar rats weighing 120 g were preimmunized with 1 mg/100 g body weight (wt) of normal rabbit IgG in complete Freund's adjuvant by intracutaneous injection. Four days later, rabbit AGBM antiserum, raised by standard techniques (Sterzel, R. B., Pabst, R., "The Temporal Relationship Between Glomerular Cell Proliferation and Monocyte Infiltration In Experimental Glomerulonephritis", *Virchows Archiv B*, (1982), 38, 337-344), was injected intravenously into 24 rats (GN group). Sham rats (n =12) received normal rabbit serum and served as controls.

At the time of preimmunization, 12 rats of the designated GN group were started on pellets containing nitrendipine (Nit), a dihydropyridine CEB with a content of 1 mg/g pellet (Zeigler Brothers, Gardner, Pa., U.S.A.) (GN/Nit group). The remaining 12 GN rats and all 12 sham animals were kept on the same rat pellets without Nit. The control groups were designated GN/Co and Sham/Co. respectively.

Preliminary studies showed that rats feeding on Nit containing pellets (1 mg/g) had serum levels of Nit averaging 47.2 +10.0 ng/ml when serum was obtained approximately 6 hours after feeding.

Functional studies

Body weight, systolic blood pressure (tail cuff measurements by a Doppler flowmeter), and 24 hour urinary albumin excretion (double immunodiffusion) were determined in conscious rats in weekly intervals before and after serum injection. Renal clearance studies were performed by standard techniques (Stein et al, supra; Huelsemann, J. L., Sterzel, R. B., McKenzie, D. E., Wilcox, C. S., "Effects of a Calcium Entry Blocker on Renal Function During Angiotensin-induced Hypertension in the Rat", *Hypertension*, (1985), 7, 374-379) at 4-5 weeks in rats anesthetized with "INACTIN". The glomerular filtration rate (GFR) was determined by the clearance of $^3$H-methoxy inulin in three 20-minute periods after equilibration for 1 hour. Effective renal plasma flow was measured by the clearance of para-aminohippurate (PAH). These results were used to calculate filtration fraction, renal blood flow, and total renal vascular resistance. Moreover, the excretion rate of Na was measured, and fractional excretion of $FE_{Na}$) was calculated.

Morphologic studies

At the end of the clearance study, the kidneys were perfused with a Ringer-gelatin solution, using a retrograde aortic catheter. After blanching the kidneys, one organ was removed, fixed by snap freezing in liquid nitrogen, and processed for immunofluorescence microscopy. The remaining kidney was perfused with Karnovsky's fixative and processed for light microscopy (Foellmer, et al, supra; Stein et al, supra and Sterzel, et al, supra). Renal sections were evaluated in a "blinded" fashion for histopatholgic changes using semiquantitative scores (scales neg to 4+) for immunofluorescence staining and for light microscopic abnormalities, as described in Stein, et al, supra. Percentages of glomeruli with epithelial crescents were also determined by light microscopy.

Comparison of data (mean +SEM) for the groups studied was performed using the unpaired Student test. A probability of less than 5% was considered to be statistically significant.

Results

All rats tolerated the immunization procedures well; they also tolerated the injections of AGBM serum or normal rabbit serum well. For the first two weeks of nephritis, rates of weight gain were somewhat slower in GN/Nit rats (because of slight, statistically insignificant diminution in food intake), averaging 23±4 g/day in GN/Nit, 26±3 in GN/Co, and 27±3 in Sham/Co (p>0.1). By week 2, the majority of nephritic rats looked ill and mortality occurred in weeks 3 and 4. This was clearly more frequent in GN/Co rats (6 out of 12), than in GN/Nit animals (2/12). Most dying rats showed imperssive peripheral edema and ascites.

Figure 2:
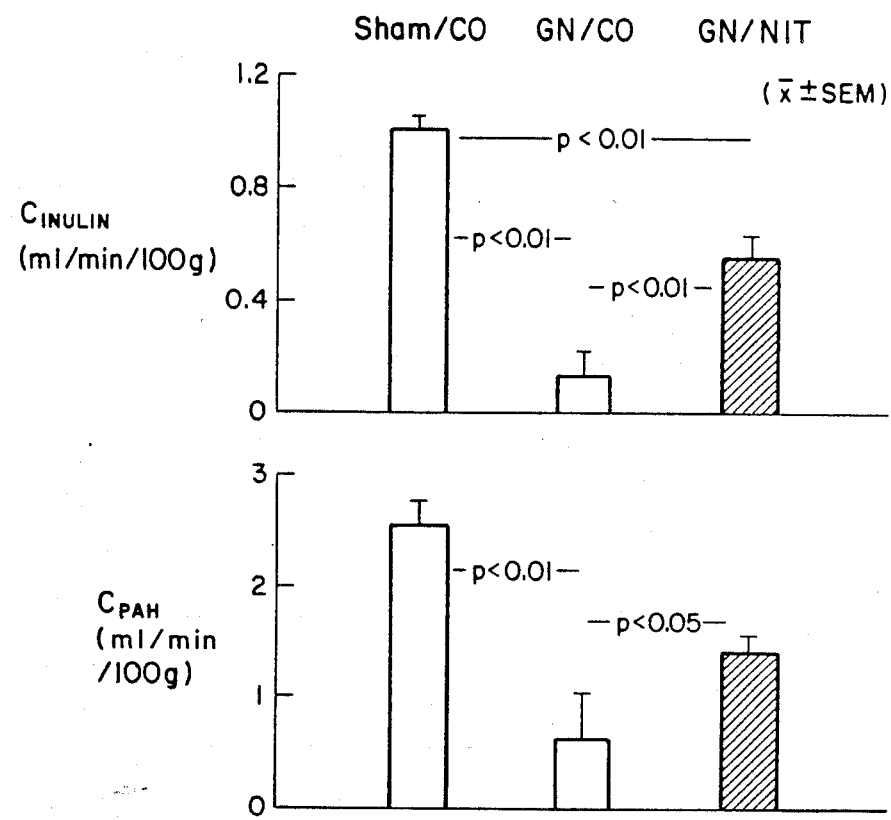
FIG. 2 depicts in two bar graphs the results on renal clearances of insulin (FIG. 2a) and of PAH (FIG. 2b) at 4 weeks of glomerulonephritis in sham animals and rats, with and without nitrendipine.

Surviving rats at week 4 underwent clearance studies. At this time body weights were GN/Nit, 295±12; GN/Co, 283±24; Sham/Co, 304±9 g (p>0.1). FIG. 1 illustrates the time courses for systolic blood pressure (sBP) and urinary albumin excretion rates ($R_{Alb}$. V). By week 3, mean sBP values for the GN/Co group was significantly higher than in GN/Nit and Sham/Co, indicating that Nit did maintain normotension in nephritic rats. Marked albuminuria developed in all rats that had received AGBM antiserum when compared to their own prenephritis control values and to the Sham/Co group. However, nephritic rats receiving Nit excreted significantly less albumin than diseased animals on a control diet. Results of the clearance experiments in anesthetized rats are depicted in FIG. 2. Means of inulin clearance ($C_{Inulin}$) and of PAH clearance ($C_{PAH}$) of nephritic rats on a control diet were severely reduced when compared to Sham/Co rats. Nit-treated GN rats had less pronounced reduction of renal function ($p > 0.05$). Calculated values for filtration fraction were lowest in GN/Co, yet this difference did not reach statistical significance compared to the other two groups.

Figure 3:
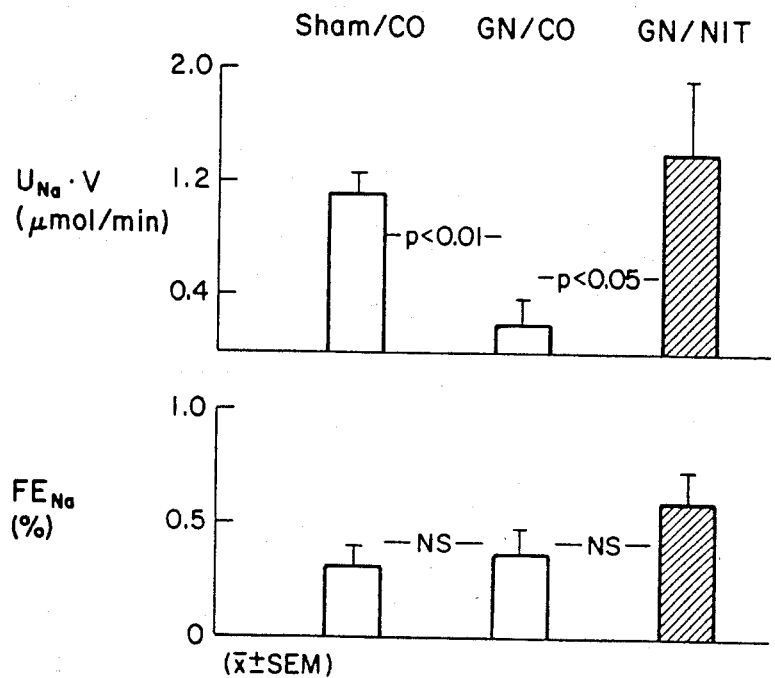
FIG. 3 depicts in two bar graphs the results from clearance studies on urinary excretion of sodium (FIG. 3a) and fractional sodium excretion (FIG. 3b) in sham animals and rats, with and without nitrendipine.

The mean hematocrit in the GN/Co group was lowest ($30.6 \pm 3.7\%$ vs $37.0 \pm 2.3\%$ for GN/Nit and for Sham/Co $42.0 \pm 3.5\%$; $p < 0.05$). Effective renal blood flow ($C_{PAH}$/1-hematocrit) was most depressed in nephritic rats on the control diet. Consequently, calculated values for total renal vascular resistance were highest in GN/Co animals reaching a mean value of $402 \pm 160$ units. Nit-treated nephritic rats had $90.2 \pm 24$, much closer to the Sham/Co group ($35.3 \pm 8$). FIG. 3 depicts data on urinary Na excretion. $U_{Na} \cdot V$ was lowest in nephritic rats on control pellets. GN/Nit had consistentcy higher $U_{Na} \cdot V$ results, not different from Sham/Co.

Immunofluorescence microscopy showed in all GN rats heavy linear staining for rabbit IgG and rat IgG along the glomerular capillary loops, as is characteristic for this model of glomerulonephritis (Foellmer, et al, supra; Stein, et al, supra, Sterzel, et al, supra). No qualitative difference in fluorescent staining activity was appreciated in GN/Co vs GN/Nit. The microscopic findings are summarized in Table 1. Table 1 is a summary of semiquantitative evaluation of morphologic changes by immunofluorescence and light microscopy (scales: negative to 4+). Averages and ranges were based on findings in rats per group.

TABLE 1

| | Renal histopatholgy | | |
|---|---|---|---|
| | Sham/co | GN/co | GN/nit |
| Glomeruli | | | |
| Immunofluorescence/ for rat IgG | Negative | 4+ | 4+ |
| Tuft hypercellularity | Negative | 3-4+ | 2-4+ |
| Tuft sclerosis | Negative | 1-3+ | 1-2+ |
| Epithelial crescents (%) | 0 | 79(61-100) | 62(26-94) |
| Interstitium Hypercellularity | Negative | Moderate to pronounced | Mild to moderate |

Figure 4:
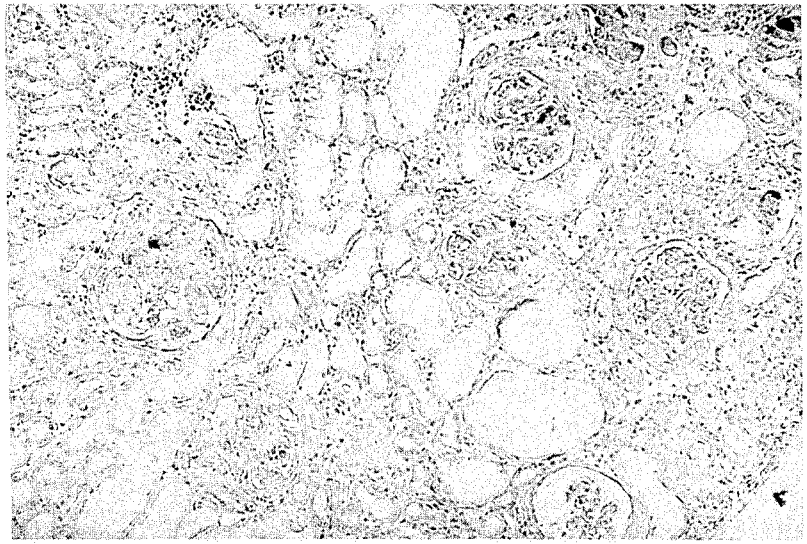
FIG. 4 is a photomicrograph of a representative renal section from a rat on control pellets at 4 weeks of AGBM glomerulonephritis. Glomeruli show marked hypercellularity of tufts segmental sclerosis, epithelial crescents and also tubulointerstitial abnormalities.

FIG. 4 shows typical histopathological alterations of a rat on control diet at 4 weeks of nephritis. Most glomeruli were clearly abnormal, showing a wide spectrum of proliferative changes of tufts, and formation of epithelial crescents and adhesions. In addition, a portion of glomeruli had advanced segmental sclerosis. Nephritic rats also showed marked, albeit irregular, widening of the interstitial spaces with focal hypercellularity and/or fibrosis. Tubular changes included protein casts, focal widening of lumina, and epithelial attenuation or atrophy. By light microscopy, there were no significant vascular alterations. While the Nit-treated nephritic rats showed a tendency to less pronounced renal abnormalities, the variability of histopathologic changes did not allow statistical analysis of these qualitative observations.

It was found that continuous oral administration of the dihydropyridine CEB, nitrendipine, attenuated some of the renal abnormalities of AGBM glomerulonephritis. During the 4-week course of standardized immunological model of nephritis, overall mortality was reduced, renal loss of albumin was diminished, and onset of systemic hypertension was prevented. Moreover, after 4 weeks of disease, reduction of renal function, as determined by clearance methods in anesthetized rats, was much less pronounced in Nit-treated nephritic animals. Administration of the Nit blunted the striking rise of total renal vascular resistance seen in nephritic control rats, associated with more effective maintenance of renal blood flow. GFR appeared protected. The available results on whole kidney clearances do not allow precise analysis of mechanisms responsible for the observed GFR-sparing effect noted in Nit-treated rats with nephritis.

Although it is conceivable that renal vasodilation may have played a contributory role in the observed beneficial effect of nitrendipine, it is presently felt that other factors may be even more important in the protective acitivity of nitrendipine in experimental glomerulonephritis. This assumption is based on the following:

(1) No renal vasodilators were heretofore described to protect animals from functional changes associated with glomerulonephritis.

(2) Nitrendipine was described to inhibit antigen-induced histamine release from basophils (see Busse et al., above).

(3) CEBs, including nitrendipine, are known to prevent $Ca^{2+}$ overload in various tissues.

It will be appreciated that the instant specification and claims are set forth by way of illustration and not limitation, and that various modifications and changes may be made without departing from the spirit and scope of the present invention.

What is claimed is:

1. A method of treating a patient suffering from glomerulonephritis, the method comprising administering to said patient a therapeutically effective amount of nitrendipine, either alone or in admixture with a pharmaceutically acceptable diluent.

2. A method according to claim 1, wherein the nitrendipine is administered intravenously in an amount of 0.01 to 10 mg per kg body weight per day.

3. A method according to claim 1, wherein the nitrendipine is in admixture with a solid, liquid or liquefied gaseous diluent.

4. A method according to claim 1, wherein the admixture contains 0.5 to 90% of said nitrendipine.

5. A method according to claim 1, wherein the nitrindipine is in the form of a sterile physiologically isotonic aqueous solution.

6. A method according to claim 1, wherein the nitridipine is in the form of a tablet, pill, dragee, capsule, caplet, ampoule or suppository.

* * * * *